United States Patent [19]
Van Duzee

[11] 4,137,309
[45] Jan. 30, 1979

[54] THERAPEUTIC TREATMENT

[75] Inventor: Barry F. Van Duzee, Cincinnati, Ohio

[73] Assignee: The Procter & Gamble Company, Cincinnati, Ohio

[21] Appl. No.: 732,226

[22] Filed: Oct. 14, 1976

[51] Int. Cl.² .............................................. A61K 31/66
[52] U.S. Cl. .................................................... 424/204
[58] Field of Search ......................................... 424/204

[56] References Cited
U.S. PATENT DOCUMENTS
3,584,125  6/1971  Francis ................................. 424/204

OTHER PUBLICATIONS
Ann. Soc. Belge Med. Trop., (1969), 49, 2 205-210.

Primary Examiner—Frederick E. Waddell
Attorney, Agent, or Firm—Jerry J. Yetter; Filcik Julius P.; Richard C. Witte

[57] ABSTRACT

Organophosphonate compounds are used in the treatment of sickle cell anemia and other hemoglobinopathies, as well as attendant peripheral vascular diseases.

5 Claims, No Drawings

THERAPEUTIC TREATMENT

BACKGROUND OF THE INVENTION

Sickle cell anemia is a disease which potentially afflicts some 8% of Black people in the United States who have Sickle Cell Trait, and their offspring. By the present invention, organophosphonate compounds are used to treat patients suffering with sickle cell anemia and related hemoglobinopathies and attendant peripheral vascular diseases.

Sickle cell anemia is one type of hemoglobinopathy whose origin has been traced to genetic defects. Sickle cell anemia is characterized by the formation of abnormal hemoglobin (HbS) and its inclusion in the erythrocytes (red blood cells) of people afflicted with this disease. The normal (non-sickle cell) erythrocyte is oxygenated in the lungs and travels through ever-narrowing blood vessels to the microvasculture (capillary bed) where oxygen delivery to the tissues is carried out. When entering the microvasculature, the erythrocytes must be able to pass through capillary channels which are narrower than the erythrocyte cells, themselves. Accordingly, the erythrocytes must be deformable so that passage through the narrowest capillary openings can occur, prior to return of the erythrocytes to the heart. In sickle cell anemia, the erythrocytes lack the normal deformability of healthy red blood cells. Accordingly, patients afflicted with this disease suffer gradual attrition due to luminal occlusion of small vessels by sickle cell erythrocytes in various stages of reversible and irreversible deformation. In short, frank entrapment of the non-deformable, sickle-shaped erythrocytes in the microvasculature occurs.

The clinical aspects of children suffering with sickle cell disease include a marked increase of pneumonia, diarrhea, urinary tract infection, meningitis, massive sepsis, and osteomyelitis, as compared with the non-sickle cell population. As might be expected with a disease state involving the microvasculature, thrombotic crises occur with some regularity, and pain, swelling and tenderness of various afflicted appendages occasioned by poor circulation are common.

In the sickle cell, itself, it appears that the cell membrane has somehow been damaged and is stiff and less deformable than normal, healthy erythrocytes. Other than the recognition that sickle cell anemia is an inheritable, genetic disease, little else is known of its etiology. Some workers have suggested that sickle cell erythrocytes are excessively permeable to calcium and that, somehow, the attachment of calcium to the endoface of the erythrocytes enhances their irreversible deformation characteristics.

Various organophosphonate compounds have recently been reported to be useful in the treatment of disease states involving anomalous mobilization and deposition of calcium phosphate salts, as occurs in osteoporosis and Paget's Disease (osteitis deformans). By the present invention, organophosphonate compounds are employed in the treatment of patients afflicted with sickle cell disease.

Quite surprisingly, moderate high levels of the organophosphonates in the blood do not appear to beneficially enhance the deformability of the sickle cell erythrocytes to the same extent as somewhat lower blood levels. Of course, the dose/response profiles of individual patients may vary somewhat. In any event, the present invention is based on the discovery that the organophosphonates restore the deformability of the sickled erythrocytes.

RELATED REFERENCES

A wide variety of organophosphonate compounds and their use in the treatment of disease states involving the anomalous mobilization and deposition of calcium phosphate in animal tissue are disclosed in U.S. Pat. No. 3,683,080, M. D. Francis, issued Aug. 8, 1972. The other U.S. and foreign patents cited hereinafter also disclose organophosphonate compounds and their use in the treatment of similar disease states.

The copending U.S. patent application of Francis, entitled "THERAPEUTIC COMPOSITION," Ser. No. 685,969, filed May 13, 1976, discloses the use of organophosphonate compounds in the treatment of ischemic tissue diseases, which can include those caused by certain types of anemia.

The foregoing references relate to various medical and veterinary use of organophosphonate compounds of the type employed herein. The present invention is based on the discovery that the organophosphonates normalize the deformation properties of red blood cells and are thus useful in the treatment of various blood diseases (hemoglobinopathies) characterized by abnormally rigid red blood cells. Sickle cell anemia is one such disease state which can be treated in the manner of this invention.

Background material on sickle cell anemia appears in the text SICKLE CELL ANEMIA AND OTHER HEMOGLOBINOPATHIES, R. D. Levere, Ed., Academic Press, 1975.

The effects of prostaglandin drugs on the filterability of red blood cells is reported by Allen and Rasmussen, Science, 74, 514 (1971).

SUMMARY OF THE INVENTION

The present invention encompasses a process for substantially normalizing the deformability of red blood cells comprising administering to patients in need of such treatment a safe and effective amount of an organophosphonate compound of the type disclosed hereinafter. The process of this invention is especially useful for treating human patients afflicted with sickle cell anemia, and is also useful in the treatment of other hemoglobinopathies characterized by red blood cells with abnormal deformation properties.

The process of this invention employs pharmaceutically-acceptable organophosphonate compounds, especially diphosphonate compounds, in a therapeutic regimen. The geminal diphosphonate compounds disclosed hereinafter, especially ethane-1-hydroxy-1,1-diphosphonic acid, its pharmaceutically-acceptable salts and esters, methanediphosphonic acid, its pharmaceutically-acceptable salts and esters, and methanedichlorodiphosphonic acid, and its pharmaceutically-acceptable salts and esters are preferred for use in this invention.

It is to be understood that the present process does not appear to correct the genetic defect which causes hemoglobinopathis such as sickle cell anemia. Rather, the organophosphonate compounds seem to act directly on the afflicted red blood cells to normalize their deformation properties and bring them more in line with healthy cells, thereby providing an effective therapeutic regimen.

DETAILED DESCRIPTION OF THE INVENTION

Administering organophosphonates to patients afflicted with hemoglobinopathies involving reduced deformability of red blood cells substantially normalizes the deformability of the cells and provides an effective therapeutic regimen.

By "administration" of the organophosphonate compounds herein is meant systemic use, as by injection (especially parenterally), intravenous infusion, and oral administration thereof, as well as by extracting portions of the patient's blood, contacting the blood with organophosphonate, and transfusing the blood back into the patient's bloodstream.

By "substantially normalizing the deformability of red blood cells" means that cells, especially sickle cells, are rendered more like normal red blood cells with regard to their ability to pass through the microvasculature of the body. The deformation properties of red blood cells can be measured by ultrafiltration techniques, as described more fully hereinafter.

By an "effective amount" of the organophosphonate compound herein is meant an amount of the compound sufficient to achieve the desired therapeutic result, i.e., normalization of the deformability of the red blood cells in a patient in need of such treatment. It will be appreciated that the amount of the organophosphonate compound employed in any treatment regimen will vary, depending on the patient, the severity of the disease state, and like factors which must be considered by the attending physician.

By a "safe" amount of the organophosphonate compound herein is meant that the benefit:risk ratio attendant with the administration of any drug composition is judged to be acceptable, according to the precepts of sound medical practice. Typical dosage levels to be used in the present process are disclosed in more detail hereinafter, but it is to be understood that these can be modified by the attending physician according to the needs of individual patients.

By "pharmaceutically-acceptable" herein is meant that the specified ingredients are suitable for systemic administration to humans without undue toxicity, irritation, allergic response, and the like, commensurate with a reasonable benefit:risk ratio.

By the term "comprising" herein is meant that various other, compatible drugs and medicaments can be conjointly employed in the process of this invention as long as the critical organophosphonate compounds are used in the manner disclosed herein. For example, the patient may continue to receive various analgesics, diuretics, etc., concurrently with the administration of the organophosphonate compounds. The term "comprising" thus encompasses and includes the more restrictive terms "consisting of" and "consisting essentially of" which characterize the use of the essential organophosphonate compounds in the manner disclosed herein.

All percentages herein are by weight, unless otherwise specified.

The organophosphonate compounds (or, more succinctly, "phosphonates") employed in the manner of this invention are of the following type.

The phosphonate compounds which can be employed in the present invention are characterized by the phosphonate moiety ($-PO_3M_2$, wherein M represents H or a pharmaceutically-acceptable cation or ester group). The phosphonates herein are organophosphonates, i.e., the phosphonate moiety is attached to a carbon atom by a carbon-phosphorus bond (C—P bond). The carbon atom, in turn, is bonded to other hydrocarbyl groups, e.g., alkyl phosphonates, or to hydrogen atoms, e.g., methane phosphonates, or to mixed hydrocarbyl groups, hydrogen atoms or other substituents, e.g., haoalkyl phosphonates. The hydrocarbyl groups can be substituted or non-substituted alkyl (including cycloalkyl), aryl (including heteroaryl) and the like. Substituent groups on the alkyl or aryl hydrocarbyl moiety can be, for example, additional phosphonate moieties; halogens, especially chlorine; carboxyl; esterified carboxyl; hydroxyl; amino; amido; and the like. Preferred for use herein are organophosphonates having more than one $C-PO_3M_2$ group; diphosphonates, especially geminal diphosphonates characterized by the grouping

are most highly preferred.

Typical phosphonate compounds useful herein are of the formula

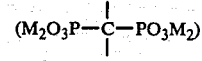

(vicinal)

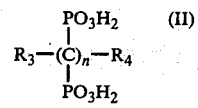

(geminal)

wherein n is an integer from 1 to about 10 and the substituent groups are H, alkyl, aryl, alkenyl, and the like. Examples of type I phosphonates are those wherein R, $R_1$ and $R_2$ are each hydrogen, alkyl, $-CH_2OH$ or are as noted for groups $R_3$ and $R_4$. Examples of type II phosphonates are those wherein $R_3$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., chlorine, bromine, and fluorine), amino, substituted amino (e.g., dimethylamino, diethylamino, N-hydroxy-N-ethylamino, acetylamino), $-CH_2COOH$, $-CH_2PO_3H_2$, $-CH(PO_3H_2)$ (OH) or $-CH_2CH(PO_3H_2)_2$; $R_4$ is hydrogen, lower alkyl (e.g., methyl, ethyl, propyl, and butyl), amino, benzyl, halogen (e.g., chlorine, bromine and fluorine), hydroxyl, $-CH_2COOH$, $-CH_2PO_3H_2$, or $-CH_2CH_2PO_3H_2$, or a pharmaceutically-acceptable salt thereof such as alkali metal (e.g., sodium and potassium), alkaline earth metal (e.g., calcium and magnesium), non-toxic heavy metal (e.g., stannous and indium), and ammonium or low molecular weight substituted ammonium (e.g., mono-, di-, and tri-ethanolammonium) salts. It will be appreciated that groups R, $R_1$ and $R_2$ and groups $R_3$ and $R_4$ can be cycloalkyl, heterocyclic or can be joined in ring structures, said rings being carbocyclic or heterocyclic.

The above described organophosphonic acids and their pharmaceutically-acceptable salts and esters are commonly referred to collectively as "phosphonates," "disphosphonates" or "polyphosphonates."

Operable phosphonates of the above formula (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid; nonane-1,2,3,4,5,6,7,8,9-nonaphosphonic acid; decane-1,2,3,4,5,6,7,8,9,10-decaphosphonic acid; and the pharmaceutically acceptable salts of these acids, e.g., sodium, potassium, calcium, magnesium, ammonium, triethanolammonium, diethanolammonium, and monoethanolammonium salts.

Among the operable phosphonates encompassed by the above formula (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid (dichloromethylene diphosphonic acid); nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphonoprop-2-ene; octane-1,1-diphosphonic acid; dodecane-1,1-diphosphonic acid; phenylaminomethanediphosphonic acid; maphthylaminomethanediphosphonic acid; N,N-dimethylaminomethanediphosphonic acid; N-(2-hydroxyethyl)-aminomethanediphosphonic acid; N-acetylaminomethanediphosphonic acid; aminomethanediphosphonic acid; and the pharmaceutically-acceptable salts of these acids, e.g., sodium, potassium, calcium, magnesium, stannous indium, ammonium, triethanolammonium, diethanolammonium, and monoethanolammonium salts.

Mixtures of any of the foregoing phosphonic acids, and/or salts can be used in the practice of this invention.

The geminal diphosphonates of formula (II) are most preferred for use herein.

Ethane-1-hydroxy-1,1-diphosphonic acid, an especially preferred geminal phosphonate, has the molecular formula $CH_3C(OH)(PO_3H_2)_2$ (according to nomenclature by radicals, the acid might also be named 1-hydroxyethylidene diphosphonic acid). The most readily crystallizable salt of this acid is obtained when two or three of the acid hydrogens are replaced by sodium. Preferred salts for the purpose of this invention are the trisodium hydrogen salt which has the structure:

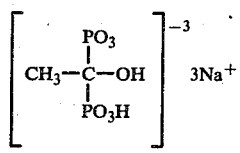

and the disodium dihydrogen salt.

The trisodium hydrogen salt normally crystallizes as the hexahydrate which loses some water during air-drying to yield a mixture of the hexa- and monohydrate averaging 3 to 4 molecules of water of hydration.

While any pharmaceutically-acceptable salt of ethane-1-hydroxy-1,1-diphosphonic acid can be used in the practice of this invention, the tetrasodium salt, the trisodium hydrogen salt, the disodium dihydrogen salt, the monosodium trihydrogen salt, and the mixtures thereof are preferred. The other sodium, potassium, ammonium, and mono-, di-, and tri-ethanolammonium salts and mixtures thereof are also suitable, provided caution is observed in regulating the total intake of cation species in the salt composition. These compounds can be prepared by any suitable method; however, an especially preferred method is disclosed in U.S. Pat. No. 3,400,149, Sept. 3, 1968, incorporated herein by reference.

Methanehydroxydiphosphonic acid and related compounds operable herein can be prepared, for example, by the reaction of phosgene with an alkali metal dialkylphosphite. A complete description of these compounds and the method for preparing same is found in U.S. Pat. No. 3,422,137, O. T. Quimby, incorporated herein by reference.

Methanediphosphonic acid and related compounds useful herein are described in detail in U.S. Pat. No. 3,213,030, granted Oct. 19, 1965; a preferred method of preparing such compounds is disclosed in U.S. Pat. No. 3,251,907, granted May 17, 1966, incorporated herein by reference.

Ethane-1,1,2-triphosphonic acid and related compounds which can be used in this invention, as well as a method for their preparation, are fully described in U.S. Pat. No. 3,551,339, O. T. Quimby, incorporated herein by reference.

Propane-1,1,3,3-tetraphosphonic acid and related compounds herein, and a method for preparing same are fully disclosed in U.S. Pat. No. 3,400,176, O. T. Quimby, incorporated herein by reference.

Pentane-2,2-diphosphonic acid and related compounds can be prepared in accordance with the method described by G. M. Kosolopoff in *J. Amer. Chem. Soc.* 75, 1500 (1953), incorporated herein by reference.

Propane-1,2,3-triphosphonic acid and salts thereof can be prepared by a process disclosed in the application of D. Allen Nicholson and Darrel Campbell, Ser. No. 694,002, filed Dec. 27, 1967, now abandoned.

Butane-1,2,3,4-tetraphosphonic acid and salts thereof can be prepared by a process disclosed in the application of D. Allan Nicholson and Darrel Campbell, Ser. No. 694,003, filed Dec. 27, 1967, now abandoned.

The higher aliphatic vicinal polyphosphonates and salts thereof can be prepared by the process disclosed in U.S. Pat. No. 3,584,035, Nicholson and Campbell, incorporated herein by reference.

Substituted ethane diphosphonic acids and salts and esters thereof are disclosed in U.S. Pat. No. 3,940,436, issued Feb. 24, 1976, to A. F. Kerst, the disclosures of which are incorporated herein by reference. U.S. Pat. No. 3,944,599, to the same inventor, discloses geminal diphosphonate compounds having halogen and hydroxyl substituent groups, and the means for preparing same. The disclosures of this patent are also incorporated herein by reference.

Phosphonobutane tri- and tetra-carboxylic acid compounds and their preparation are disclosed in U.S. Pat. Nos. 3,886,204 and 3,886,205. both issued May 27, 1975, to Geffers, et al., the disclosures of which are incorporated herein by reference.

German 2360-798, June 26, 1975, to Henkel & Cie GmbH discloses pharmaceutical and cosmetic preparations for influencing the deposition of poorly soluble calcium salts, said preparations comprising polymethylene phosphonic acid compounds. This publication, the disclosures of which are incorporated herein by reference, describes the preparation of the phosphonate materials in detail.

The preparation and pharmacological properties of various amino phosphonate compounds are described in German 2343-146 (Mar. 6, 1975); Belgian 822-930 (June 4, 1975); Belgian 822-929 (Dec. 6, 1973); German 2360-711 (June 12, 1975); German 2360-719 (June 6, 1975); Belgian 819-187 (Feb. 26, 1975); Belgian 819-188 (Feb. 26, 1975); and Belgian 819-189 (Feb. 26, 1975), the disclosures of said publications being incorporated herein by reference.

As can be seen from the foregoing, the preparation of the phosphonates used in the practice of this invention can be accomplished using well-known methods, or by simple modifications of various art-disclosed procedures. Only those organophosphonates which are pharmaceutically-acceptable (i.e., provide a satisfactory benefit:risk ratio) are contemplated for use herein. The well-known toxicity of some type (I) monophosphonates (n=1) disclosed in the structural formulas above precludes their use herein. However, such materials are known in the art and are easily avoided in the practice of this invention.

The following demonstrates the test procedures whereby the effectiveness of the phosphonate compounds in normalizing the deformability of red blood cells from human sickle cell patients is demonstrated. Briefly, the procedure involves treating the cells with test or control agents, "tagging" the cells with a radionuclide to provide a means for quantifying the cells, and filtering the cells through membranes whose pore size is smaller than the cell diameter. Since the cells must be deformable to pass through the pores, the filterability of the cells provides a measurement of their deformability.

It will be appreciated that the filtration test can be used by an attending physician to determine the precise dosage regimen of organophosphonate compound which will normalize the deformability of red blood cells in individual patients in need of such treatment.

EXPERIMENTAL PROCEDURE

Normal red blood cells are approximately 7.2μ (microns) in diameter. Because of the deformability of normal red blood cells, they are able to pass easily through a 5μ NUCLEPORE filter. In contrast, the rigid sickled cell does not possess the deformability necessary to pass through the 5μ filter. The experimental procedure hereinafter uses the "filterability" of red blood cells in sickle cell blood to determine the effect of agents on the deformability of the sickle cells. The procedure employs a negative control (treatment of the cells with saline), a positive control (treatment of the cells with potassium cyanate, which is currently the best known treatment for sickle cell anemia, but which is toxic) and treatment of the cells with a representative organophosphonate compound of the type disclosed herein.

Heparinized whole blood drawn from sickle cell anemia patients is employed in the procedure. The sickled blood sample is mixed to produce a homogeneous dispersion of red blood cells and a micro-aliquot is used to determine the hematocrit of the blood sample. The anemic blood is centrifuged at approximately 5000 rpm for 5 minutes in a conventonal centrifuge. Blood plasma is removed and discarded and 6–7 mls. of isotonic phosphate buffer saline solution are added to ca. 2–3 mls. of the packed cells. The cells are washed with the isotonic solution to remove residual plasma. The cells are again centrifuged and washed; this washing process is repeated three times. Before centrifuging the final wash, a micro-hematocrit is taken and the volume of the suspended cells is measured by drawing the suspension into a 10 ml. graduated pipette. The suspension of cells is then equally divided into three separate 10 ml. test tubes. The divided cell suspensions are then centrifuged as before and the supernatant is discarded.

According to the procedure for radiolabeling red blood cells, J. Lab. Clin. Med. 85, 445 (1975), the three separate test tubes, each containing the same amount of cells, are then mixed with an isotonic phosphate buffered solution (pH 7.4) containing glucose and albumin, together with NaCl (negative control), KNCO and NaCl (positive control) or test organophosphonate and NaCl (test compound). Based on the hematocrit of the suspension in the final washing, a volume of appropriate isotonic solution is added to each test tube to yield a final hematocrit of 1.0.

100 Microcuries of $^{51}Cr$ are then added to each test tube by micro-pipette. The test tubes are then placed in a shaker bath at 37° C and gently agitated for one hour. At the end of this incubation period, the test tubes are removed from the shaker bath, centrifuged as before, and the radioactive supernatant liquids are removed. The cells are now labeled with radioactive chromium. The cells are washed three times, as before, each time removing the supernatants after centrifuging. The chromium-labeled treated sickle cells are then suspended in 5 ml. of isotonic phosphate-buffered saline solution. A hematocrit is taken by micro methods to determine the final sickle cell concentration. The radiolabeled sickle cells are then suspended with compatible normal cells, type O positive, in a ratio of 1:9 to a final hematocrit of 1% in isotonic phosphate-buffered saline solution in all three legs of the experiment.

The final cell suspension contains 1% cells in an isotonic phosphate-buffered saline solution. Of the 1% total cells, one-tenth of the cells are $^{51}Cr$-labeled sickle, and nine-tenths of the cells are compatible normal cells, type $O^+$. The hematocrit of the cell suspension determines the volume of cell solutions to be measured into a volumetric flask prior to a final dilution to 200 mls. with isotonic solution.

An aliquot is removed from each of the three 200 ml. volumetric flasks containing the 1% cell suspensions and submitted for radiochemical analyses. At this point, 50 mls. are removed from the negative control volumetric flask and placed in an equilibration chamber to equilibrate with the gas phase in which the partial pressure of oxygen is 26 mm. Hg. After 15 minutes of slow stirring and equilibration, a 5 ml. portion of the cell suspension is drained into a holding chamber. After completion of the draining, the cell suspension is aspirated through a 5μ NUCLEPORE filter using 10 mm. mercury pressure difference across the filter. Upon completion of the filtration (approximately 5 seconds) the vacuum is removed and the filter pad is retained for radioanalysis. The volume of the filtrate is measured in a graduated cylinder and an aliquot is submitted for radiochemical analysis.

The positive control sample and organophosphonate-treated sample are run in similar fashion. (All three samples are handled in random order in successive experiments.)

In tests of the foregoing type, the amount of radioactive red blood cells passing through the NUCLEPORE filter as compared with the amount remaining on the NUCLEPORE filter gives a measure of the deformability of the blood cells. The results are expressed as the increase in filterability of the test sample (e.g., ethane-1-hydroxy-1,1-diphosphonate) and positive control sample (KCNO) over the control (NaCl). The results from two pilot experiments of the foregoing type appear in Table I.

TABLE I

| Experiment* | Treatment | Increase in Filterability Over Control (%) |
|---|---|---|
| 1 | KCNO | 16 |
| 1 | EHDP** | 23 |
| 2 | EHDP | 38 |
| 2 | EHDP | 38 |
| 2 | KCNO | 30 |

*Experiments 1 and 2 were run at different times with the same sickel cell blood sample.
**Ethane-1-hydroxy-1,1-diphosphonic acid, disodium salt form.

The data in Table I demonstrate that the EHDP clearly has a positive effect on the filterability of sickled cells. While statistical analysis of the data is not possible due to the small number of samples, the EHDP does appear to be at least directionally superior to KCNO in increasing the filterability of sickled cells in these two pilot experiments.

Following the initial pilot experiments on the use of EHDP to affect the deformability of sickle cells, additional studies were carried out using an experimental design which was appropriate for statistical analysis. The procedure for measuring the deformability of sickle cells was as disclosed hereinabove. In these studies, the effect of the test and control agents was expressed as the percentage of cells trapped on the filter (i.e., percentage of cells remaining non-deformable) after treatment. Results from these separate studies appear in Table II.

TABLE II

| Treatment | No. of Samples | % Cells Trapped ± sd | P |
|---|---|---|---|
| Test 1 | | | |
| NaCl | 5 | 44.3 ± 11.4 | |
| KCNO (107 mM) | 5 | 13.9 ± 0.8 | < 0.01 |
| EHDP (10.7 mM) | 5 | 36.4 ± 6.7 | < 0.11 |
| Test 2 | | | |
| NaCl | 5 | 40.0 ± 4.6 | |
| KCNO (107 mM) | 5 | 11.2 ± 1.7 | < 0.01 |
| EHDP (10.7 mM) | 4 | 32.1 ± 2.3 | < 0.01 |
| Test 3 | | | |
| NaCl | 5 | 31.4 ± 5.8 | |
| KCNO (1.0 mM) | 5 | 20.2 ± 4.8 | < 0.01 |
| EHDP (1.0 mM) | 5 | 20.6 ± 6.8 | < 0.025 |

Table III hereinafter presents data showing the dose response relationship between a typical, geminal organodiphosphonate compound (EHDP) on sickled red blood cells. The data were obtained using the filtration technique described hereinabove. Tests 1, 2 and 3 appearing in Table III are the same as those from Table II. Tests 4 and 5 were additional tests which were separately run in the same manner as Tests 1-3.

As can be seen from the data appearing in Table III, relatively low concentrations of EHDP substantially normalize the deformability of human sickle cells, as measured by their filterability. Moreover, the data clearly indicate the superiority of EHDP over KCNO for sickle cell therapy. The test results, taken in conjunction with relative safety of the organophosphonates herein, as compared with the relatively high toxicity of KCNO, leads to the conclusion that the organophosphonates are a highly preferred treatment for this heretofore intractable disease state.

TABLE III

| Test No. | Treatment | No. of Samples | Treatment Concentration (mM) | % Cells Trapped ± sd | P |
|---|---|---|---|---|---|
| 1 | Control | 5 | | 10.8 ± 3.9 | |
| 1 | KCNO | 5 | 107 | 0.88 ± 0.13 | < .01 |
| 1 | EHDP | 5 | 107 | 18.7 ± 4.5 | < .01 |
| 2 | Control | 5 | | 44.3 ± 11.4 | |
| 2 | KCNO | 5 | 107 | 13.9 ± 0.8 | < .01 |
| 2 | EHDP | 4 | 10.7 | 36.4 ± 6.7 | < .11 |
| 3 | Control | 5 | | 31.4 ± 5.8 | |
| 3 | KCNO | 5 | 1.0 | 20.2 ± 4.8 | < .01 |
| 3 | EHDP | 5 | 1.0 | 20.6 ± 6.8 | < .025 |
| 4 | Control | 5 | | 58.2 ± 35 | |
| 4 | KCNO | 5 | 1.0 | 50.5 ± 11.1 | < .10 |
| 4 | EHDP | 5 | 0.10 | 44.4 ± 5.8 | < .001 |
| 5 | Control | 5 | | 33.6 ± 4.5 | |
| 5 | KCNO | 5 | 107 | 5.1 ± 0.5 | < .001 |
| 5 | EHDP | 5 | 0.01 | 57.7 ± 4.8 | < .001 |
| 5 | EHDP | 5 | 0.001 | 35.5 ± 10.9 | N.S.** |
| 5 | EHDP | 5 | 0.01* | 5.8 ± 0.6 | < .001 |

*EHDP was not removed from cell suspension after incubation.
**Not significant

For human treatment, the required dosage of organophosphonate material can vary with the type of hemoglobinopathy being treated, the severity of the condition, and the duration and treatment regimen employed. In general, single dosages can range from 0.01 mg. per kilogram to 500 mg./kg. of body weight, preferably in the range from about 0.5 mg./kg. to about 50 mg./kg., with up to four dosages daily. Higher dosages within this range are, of course, required in the case of oral administration because of limited absorption.

The organophosphonates can be administered parenterally in aqueous solution by subcutaneous, intradermal, intramuscular or intravenous injection. The usual dosage range by these modes of administration is in the range from about 0.01 to about 5 mg./kg./day.

As pointed out hereinabove, the appropriate dosage level of the organophosphonates can be tailored to the individual needs of patients by determining filterability of test red blood cells from the patients. Thus, it is within the skill of the physician to determine a dosage regimen which will yield optimal normalization of the red blood cells for individual patients.

The following examples illustrate the present invention but are not intended to be limiting thereof.

EXAMPLE I

An oral composition in tablet form comprising 200 mg. of EHDP, 40 mg. of lactose, 2.5 mg. of starch and 1.0 grams of magnesium stearate (tablet lubricant) is prepared by conventional methods.

A human patient (35 kg.) diagnosed as suffering from sickle cell anemia is treated by oral administration of four of the EHDP tablets prepared in the foregoing manner per day.

In the procedure of Example I, the EHDP is replaced by an equivalent amount of methanediphosphonic acid, sodium salt form, and methanedichlorodiphosphonic acid, sodium salt form, respectively, and used in the sickle cell anemia therapy.

EXAMPLE II

A sterile, pyrogen-free 10% solution of EHDP in physiological saline is prepared and buffered to blood pH with phosphate buffer.

A solution of the foregoing type is administered intravenously to a patient afflicted with sickle cell anemia who is in the crisis stage. Sufficient solution is administered to provide a blood level of EHDP of about 0.1 to 0.01 millimolar. The patient is maintained on this treatment until the crisis subsides. The patient is thereafter maintained on an oral dosage of EHDP, according to Example I, herein.

EXAMPLE III

A sickle cell anemia patient is treated by removing successive portions of arterial blood, incubating the blood with EHDP for a period of one hour under sterile conditions, and transfusing the patient with the thus-treated blood. In a typical procedure, the blood is treated with sufficient EHDP to provide a blood concentration in the range from about 0.5 mM to about 50 mM. Red blood cell deformability is checked periodically throughout the procedure to determine the appropriate EHDP concentration to be used. Following this treatment, the patient is maintained on oral dosages of EHDP, according to the procedure of Example I, herein.

In the process of Example III, the EHDP is replaced by an equivalent amount of propane-1,2,3-triphosphonic acid, sodium salt; hexane-1-hydroxy-2,3,4,5,6-pentaphosphonic acid, potassium salt; methanediphosphonic acid, sodium salt; and methanedichlorodiphosphonic acid (buffered to neutrality with potassium phosphate buffer), respectively, to normalize the deformability of red blood cells.

The process of Example III is performed in like fashion in the treatment of sickle cell $\beta$-thalassemia.

What is claimed is:

1. A process for treating sickle cell anemia comprising administering to patients in need of such treatment a safe and effective amount of a geminal diphosphonate compound.

2. A process according to claim 1 wherein the geminal diphosphonate compound is a member selected from the group consisting of ethane-1-hydroxy-1,1-diphosphonic acid, and the pharmaceutically-acceptable salts and esters thereof.

3. A process according to claim 2 wherein the geminal diphosphonate compound is a sodium salt of ethane-1-hydroxy-1,1-diphosphonic acid.

4. A process according to claim 1 wherein the geminal diphosphonate compound is a member selected from the group consisting of methanediphosphonic acid, and the pharmaceutically-acceptable salts and esters thereof.

5. A process according to claim 1 wherein the geminal diphosphonate compound is a member selected from the group consisting of methanedichlorodiphosphonic acid, and the pharmaceutically-acceptable salts and esters thereof.

* * * * *